(12) United States Patent
Sahatjian et al.

(10) Patent No.: US 6,565,530 B2
(45) Date of Patent: May 20, 2003

(54) IMMOBILIZING OBJECTS IN THE BODY

(75) Inventors: Ronald Sahatjian, Lexington, MA (US); Sheng Ping Zhong, Northboro, MA (US); James Wagner, Sudbury, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 4 days.

(21) Appl. No.: 09/795,635

(22) Filed: Feb. 28, 2001

(65) Prior Publication Data

US 2002/0120237 A1 Aug. 29, 2002

(51) Int. Cl.$^7$ .................................. A61F 7/12
(52) U.S. Cl. ............... 604/113; 604/93.01; 604/164.08; 606/127; 606/128
(58) Field of Search ............... 604/48, 93.01, 604/113, 164.08; 606/22, 27, 127, 128

(56) References Cited

U.S. PATENT DOCUMENTS

| | | | |
|---|---|---|---|
| 3,882,036 A | | 5/1975 | Krezanoski et al. |
| 4,188,373 A | | 2/1980 | Krezanoski |
| 4,478,822 A | | 10/1984 | Haslam et al. |
| 4,542,542 A | | 9/1985 | Wright |
| 4,696,297 A | | 9/1987 | Pleines et al. |
| 4,997,435 A | * | 3/1991 | Demeter ............ 606/127 |
| 5,147,923 A | | 9/1992 | Mueller |
| 5,330,768 A | | 7/1994 | Park et al. |
| 5,348,746 A | | 9/1994 | Dong et al. |
| 5,430,104 A | | 7/1995 | Siol et al. |
| 5,444,097 A | | 8/1995 | Tkacik |
| 5,484,610 A | | 1/1996 | Bae |
| 5,542,928 A | * | 8/1996 | Evans et al. ............ 604/113 |
| 5,702,717 A | | 12/1997 | Cha et al. |
| 5,861,174 A | | 1/1999 | Stratton et al. |
| 5,958,443 A | | 9/1999 | Viegas et al. |
| 6,096,727 A | | 8/2000 | Kuo et al. |
| 6,152,943 A | | 11/2000 | Sawhney |

OTHER PUBLICATIONS

Brink et al., (Apr. 1983) "Glomerular Filtration in the Isolated Perfused Kidney. I. Sieving of Macromolecules," *Pflugers Arch*, vol. 397(1), pp. 42–47.

Abe et al., (Aug. 1990) "Evaluation of Pluronic F127 as a Base for Gradual Release of Anticancer Drug," *Gan To Kagaku Ryoho*, vol. 17, pp. 1546–1550. (abstract in English).

Miyazaki et al., (Jun. 1995) "Percutaneous Absorption of Indomethacin from Pluronic F127 Gels in Rats," *Journal of Pharmaceutical Pharmacology*, vol. 47(6), pp. 455–457.

Batrakova et al., (Nov. 1996) "Antharacycline Antibiotics Non–Covalently Incorporated Into the Block Copolymer Micelles: In Vivo Evaluation of Anti–Cancer Activity," *British Journal of Cancer*, 74(10): 1545–52.

R. Dagani, (Jun. 1997) "Intelligent Gels: Using Solvent–Swollen Polymer Networks that Respond to Stimuli, Scientists are Beginning to Develop a Soft, Wet, Organic Technology" *Chemical & Engineering News*.

Wirtanen et al., (Dec. 1998) "Performance Evaluation of Disinfectant Formulations Using Poloxamer–Hydrogel Biofilm–Constructs," *Journal of Applied Microbiology*, vol. 85(6), pp. 965–71.

(List continued on next page.)

Primary Examiner—Steven J. Ganey
(74) Attorney, Agent, or Firm—Testa, Hurwitz & Thibeault, LLP

(57) ABSTRACT

Stabilizing an object in the body of a patient involves the injection of a lower critical solution temperature (LCST) material in a flowable form into the body of the patient so that the material contacts the object. The LCST material then forms a gel in the body due to a temperature inside the body such that the object is contained at least partially within the gel and thereby stabilized by the gel such that the object can then be easily fragmented within the body and/or retrieved from the body.

39 Claims, 11 Drawing Sheets

OTHER PUBLICATIONS

Gilbert et al., (Dec. 1998) "The Use of Poloxamer Hydrogels for the Assessment of Biofilm Susceptibility Towards Biocide Treatments," *Journal of Applied Microbiology*, vol. 85(6), pp. 985–90.

Desai et al., (Oct. 1998) "Evaluation of Pluronic F127–Based Sustained–Release Ocular Delivery Systems for Pilocarpine Using the Albino Rabbit Eye Model," *Journal of Pharmaceutical Science*, vol. 87(10), pp. 1190–5.

Scherlund et al., (Jan. 2000) "Thermosetting Microemulsions and Mixed Micellar Solutions as Drug Delivery Systems for Periodontal Anesthesia," *International Journal of Pharmacy*, vol. 194(1), pp. 103–16.

Moore et al., (Jul. 2000) "Experimental Investigation and Mathematical Modeling of Pluronic F127 Gel Dissolution: Drug Release in Stirred Systems," *Journal of Control Release*, vol. 67(2–3), pp. 191–202.

* cited by examiner

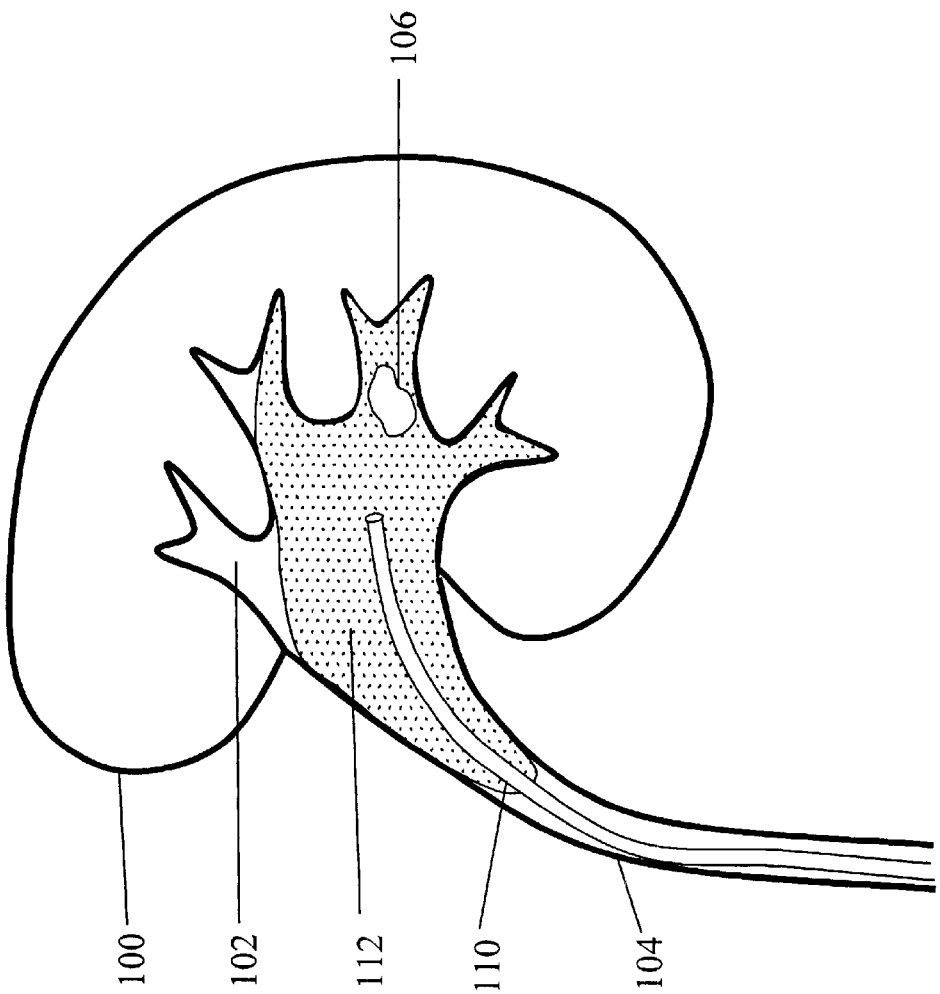

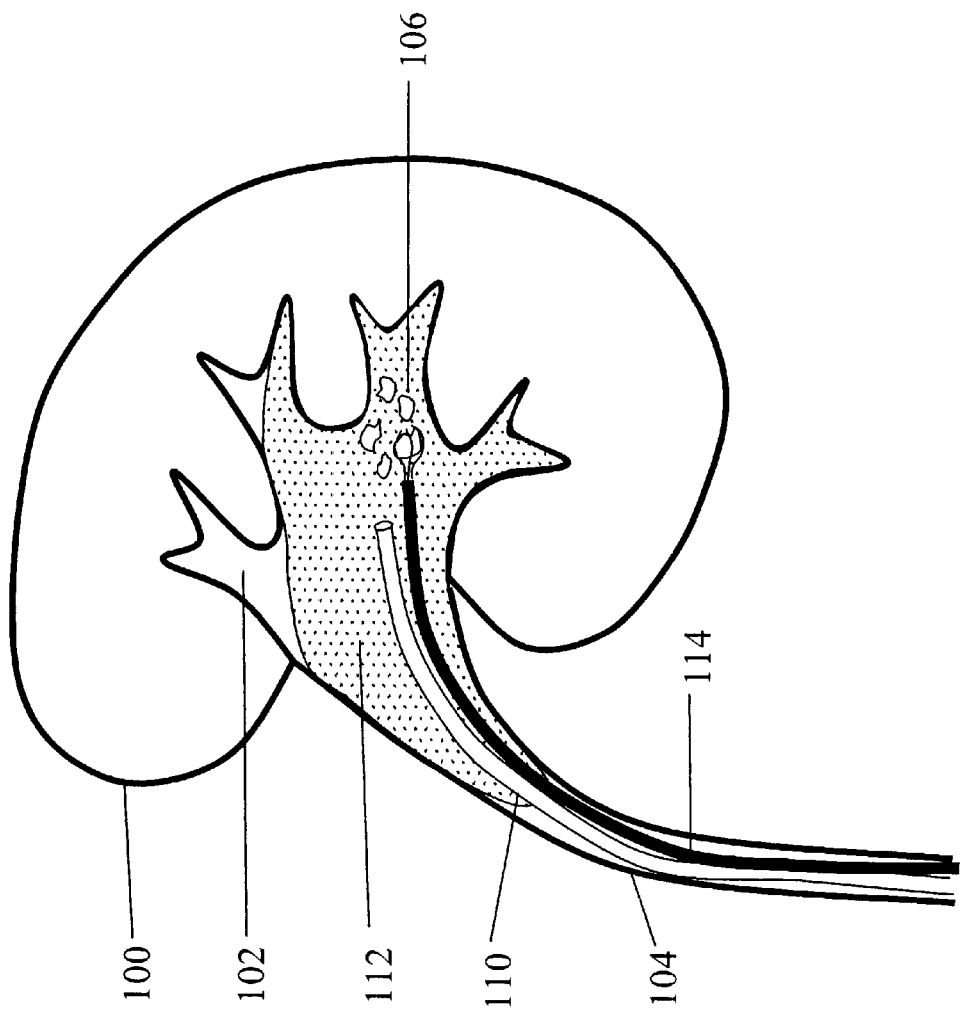

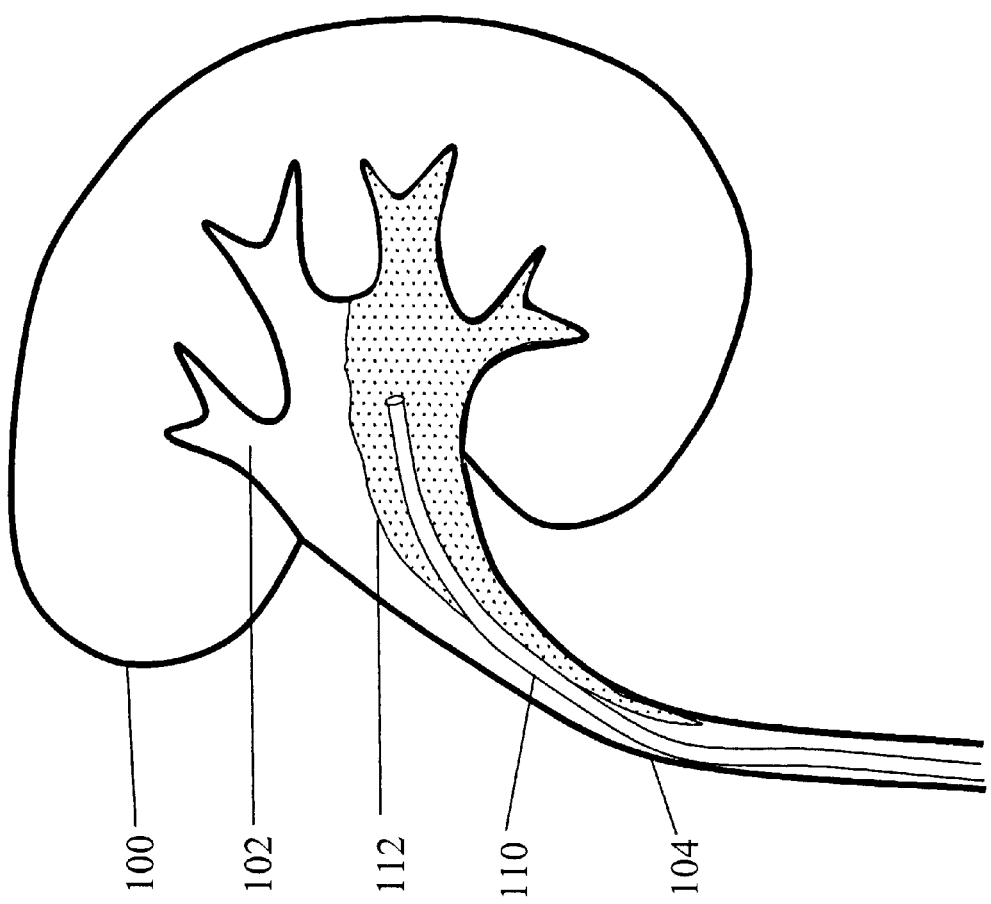

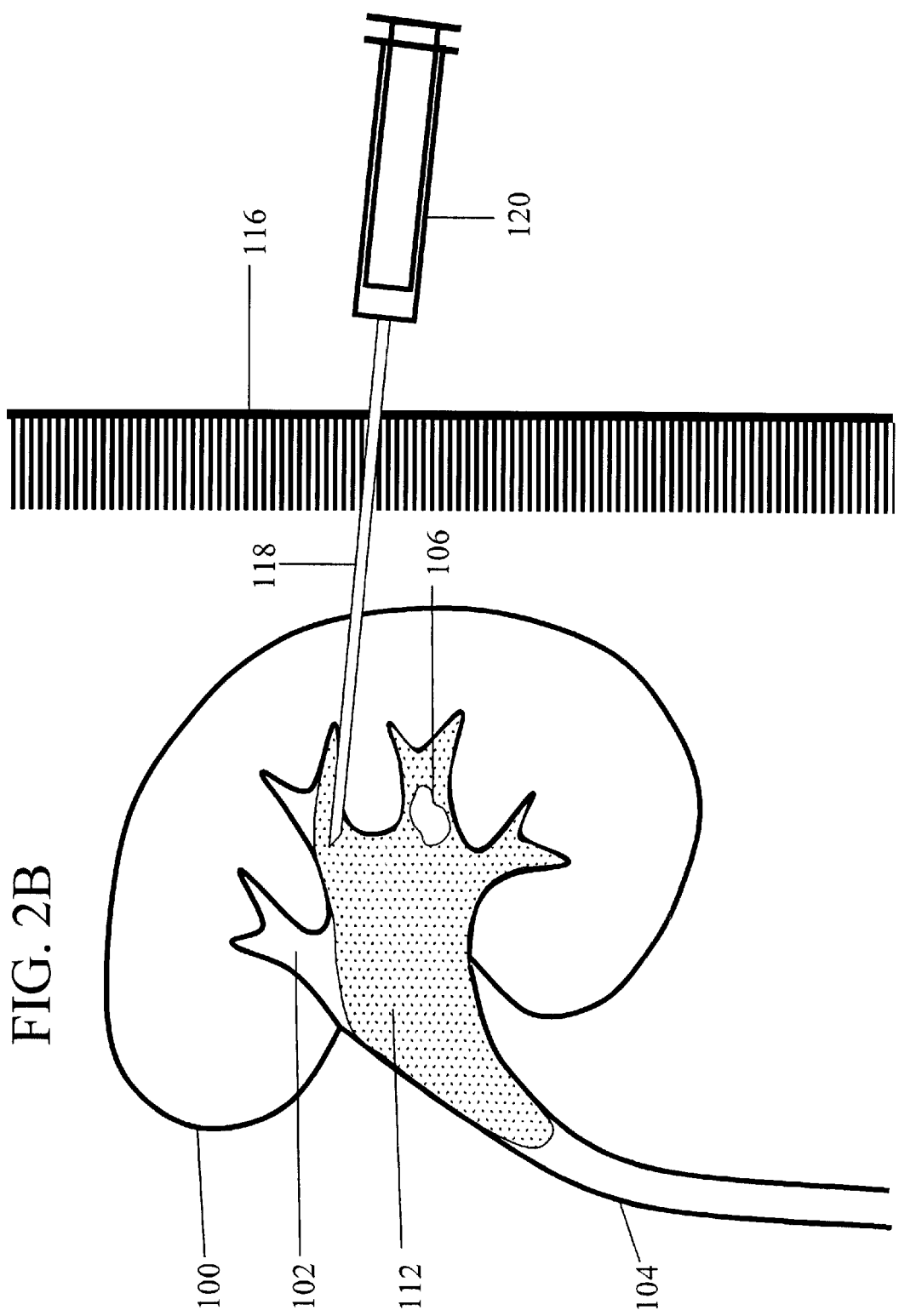

IMMOBILIZING OBJECTS IN THE BODY

TECHNICAL FIELD

This invention generally relates to medical instruments and methods for retrieving material from within a body. More particularly, the invention relates to retrieval methods, devices, and compositions for stabilizing and removing stones such as urinary tract stones, gall stones, and other objects found in the body.

BACKGROUND INFORMATION

Medical retrieval devices generally are used to retrieve biological and foreign material, such as kidney stones and other calculi, from the body of a patient. Such medical retrieval devices may be used through an endoscope or a laparoscope. The use of such devices to capture foreign material like stones is made difficult by the freedom of movement of the stones within the body. A stone may dislodge from its resting place when contacted with a retrieval device. This may cause the stone to move into an area of the body that renders the stone inaccessible or undetectable thus preventing the capture and removal of the stone.

Larger stones often need to be shattered because their size prohibits non-surgical removal from the body. Shattering a stone (by, for example, light, chemical, or physical energy) will disperse the resulting stone fragments from the original location of the stone. Stone fragments that are not removed from the body can form the nuclei for the formation of new stones. The dispersal of the fragments caused by the shattering process can cause fragments to move into inaccessible or unknown areas of the body thus preventing or interfering with the capture and removal of the fragments.

SUMMARY OF THE INVENTION

It is an object of the invention to facilitate the capture and removal of objects located within the body. The invention generally includes the use of a material that exists in liquid form at temperatures below about body temperature and as a gel at temperatures about at and above body temperature. The temperature at which the transition from liquid to gel occurs is referred to as the lower critical solution temperature (LCST), and it can be a small temperature range as opposed to a specific temperature. Materials appropriate for use according to the invention possess a LCST and are referred to as LCST materials. The methods and systems of the present invention generally involve the injection of an LCST material into a cavity or space within the body. Once inside the body, the LCST material can contact and at least partially contain an object. In many cases, the LCST will entirely envelope and surround the object. As the temperature of the LCST material rises due to the internal temperature of the body, the LCST material will reach its LCST and thus transition into the gel phase. (The specific transition point or range is determined by the specific LCST material utilized.) An object in contact with the LCST material thus will be at least partially trapped and stabilized by the gel. The stabilization of the object allows for easier capture and retrieval of the object. Stabilization of the object also allows for easier use of a lithotripsy device for fragmenting the object because the gel holds the object in place. Furthermore, the gel prevents the free dispersal of fragments of the object after the object is broken apart by the lithotripsy device. Preventing the dispersal of the fragments allows for easier capture and retrieval of the object fragments.

The invention, in one aspect, includes a method of stabilizing an object in the body of a patient. The method includes injecting a lower critical solution temperature material in a flowable form into the body of the patient to contact the object. The method further includes allowing the lower critical solution temperature material to form a gel in the body due to a temperature inside the body. The object thus is contained at least partially within the gel and stabilized by the gel.

In one embodiment according to this aspect of the invention, the method involves the use of the lower critical solution temperature (LCST) material which remains in the flowable form below about the temperature inside the body of the patient. The LCST material can form the gel about at and above the temperature inside the body of the patient.

In other embodiments, the method can include retrieving the stabilized object from the gel and/or breaking the object into at least two fragments. At least some of the fragments remain at least partially within the gel and stabilized by the gel, and these fragments can then be retrieved from the gel.

In another aspect, the invention relates to a system for stabilizing an object in the body of a patient. The system includes a lower critical solution temperature material which remains in a flowable form below about a temperature inside the body of the patient and which forms a gel about at and above the temperature inside the body of the patient. The system also includes a catheter for transferring the lower critical solution temperature material into the body in the flowable form and a guide wire for introducing the catheter into the body and guiding it to about the location of the object. The system also includes a mechanism to force the lower critical solution temperature material in the flowable form through the catheter and into the body to contact the object. The lower critical solution temperature material gels inside the body due to the temperature inside the body and thereby contains at least a portion of the object within the gel to stabilize the object.

One embodiment according to this aspect of the invention involves the use of the catheter to remove the lower critical solution temperature material from the body.

In still another aspect, the invention features a system for stabilizing an object in the body of a patient. The system includes a lower critical solution temperature material which remains in a flowable form below about a temperature inside the body of the patient and which forms a gel about at and above the temperature inside the body of the patient. The system also includes a percutaneous access device for transferring the lower critical solution temperature material into the body in the flowable form. The system further includes a mechanism to force the lower critical solution temperature material in the flowable form through the percutaneous access device and into the body to contact the object. As before the lower critical solution temperature material gels once inside the body due to the temperature inside the body and thereby contains at least a portion of the object within the gel to stabilize the object.

In one embodiment according this aspect of the invention, the percutaneous access device comprises a needle. In some embodiments, the system further includes a catheter for removing the lower critical solution temperature material from the body.

In some embodiments of this and the prior aspects of the invention, the mechanism used to force the lower critical solution temperature material into the body comprises a syringe.

The lower critical solution temperature material used in connection with all aspects of the invention can comprise a block copolymer with reverse thermal gelation properties. The block copolymer can further comprise a polyoxyethylene-polyoxypropylene block copolymer such as a biodegradable, biocompatible copolymer of polyethylene oxide and polypropylene oxide. The molecular weight of the block copolymer can be, for example, between 5,000 and 25,000, and more particularly between 7,000 and 15,000.

Also, the lower critical solution temperature material can include a therapeutic agent such as an anti-angiogenic agent.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also the drawings are not necessarily to scale, emphasis instead generally being placed upon illustrating the principles of the invention.

FIG. 1b illustrates the insertion of a catheter into the kidney by passage over the guide wire of FIG. 1a.

FIG. 1c illustrates the removal of the guide wire from the lumen of the catheter of FIG. 1b and the injection of an LCST material into the kidney through the catheter.

FIG. 1e illustrates the capture of a kidney stone fragment by a medical retrieval device such as a basket.

FIG. 1f shows the kidney after removal of the kidney stone fragments of FIGS. 1d and 1e, and after some of the LCST material has drained and/or been removed from the body.

FIG. 2b illustrates the injection of the LCST material from the syringe, through the needle, and into the kidney.

DESCRIPTION

Figure 1A:
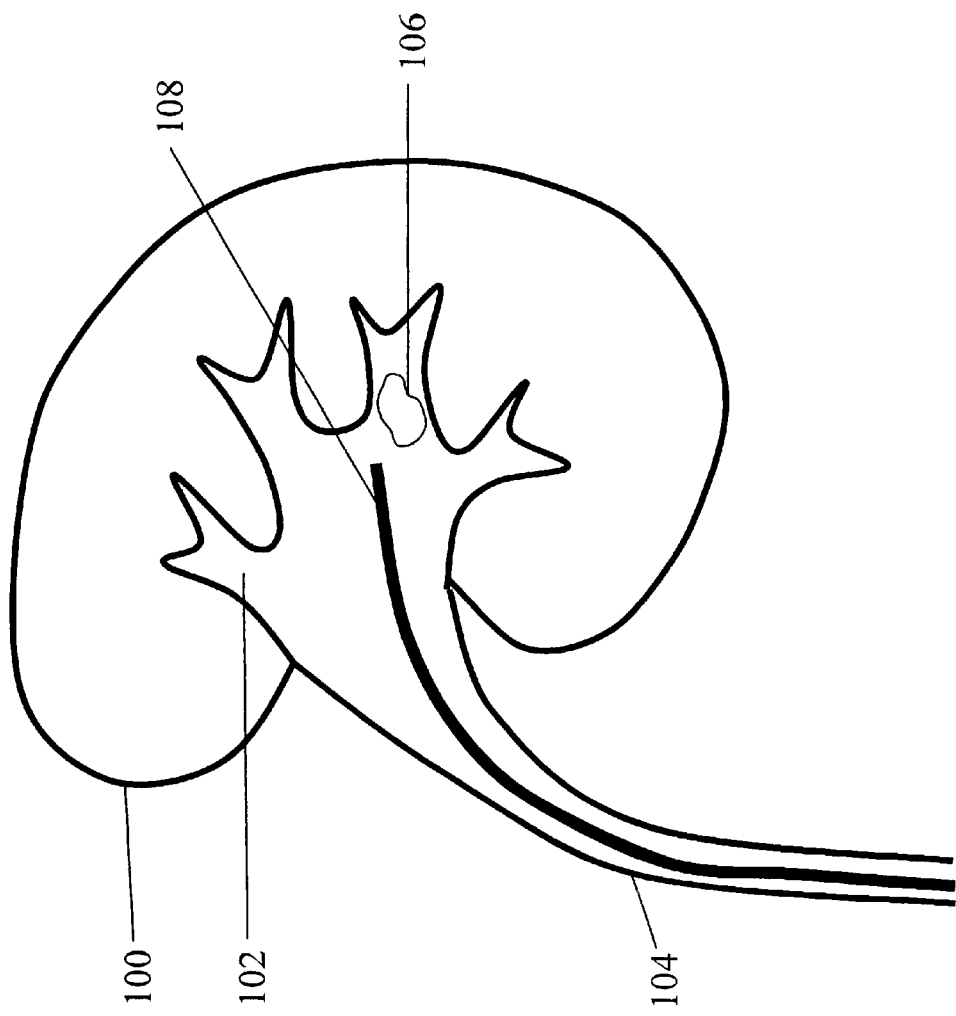
FIG. 1a illustrates the insertion of a distal end of a guide wire into a kidney containing a kidney stone.

The invention generally relates to systems and methods for stabilizing objects (such as kidney stones, gall stones, and other natural and foreign substances) found in the body of a patient (such as a human or other mammal). The invention involves the use of a material that becomes a gel at or about body temperature. The material can be injected into the body in a liquid form. The injected material once reaching body temperature undergoes a transition from a liquid to a gel. Objects that are contacted by the material become trapped entirely or partially within the gel and thus stabilized in place in the body. Medical devices for breaking the object into fragments and/or retrieving (or otherwise eliminating) the object and any of its fragments from the body can accomplish the breaking and/or removal more easily because the gel causes the object to be fixed in place and does not allow the object to move freely about the cavity in which it is located in the body. Additionally, fragments of the object that result from breaking the object with a suitable medical device (such as a laser lithotriptor) generally remain trapped at least partially within the gel, in that the gel also traps the fragments and prevents the scattering of fragments within the body. Kidney stone fragments that remain in the body can form the nuclei for the growth of other kidney stones.

Lower critical solution temperature (LCST) materials can be used in accordance with the invention. The LCST is the temperature at which LCST materials transition from liquid to gel form. Suitable LCST materials include polyoxyethylene-polyoxypropylene (PEO-PPO) block copolymers. Two acceptable compounds are Pluronic acid F127 and F108, which are PEO-PPO block copolymers with molecular weights of 12,600 and 14,600, respectively. Each of these compounds is available from BASF of Mount Olive, N.J. Pluronic acid F108 at 20–28% concentration in phosphate buffered saline (PBS) is an example of a suitable LCST material. A more preferable preparation is 22.5% Pluronic acid F108 in PBS. A preparation of 22% Pluronic acid F108 in PBS has an LCST of 37° C. Pluronic acid F127 at 20–35% concentration in PBS is another example of a suitable LCST material. A preparation of 20% Pluronic acid F127 in PBS has an LCST of 37° C. Low concentrations of dye (such as crystal violet), hormones, therapeutic agents, fillers, and antibiotics can be added to the LCST material. For example, a cancer-treating agent such as endostatin can be carried by the LCST material and thus delivered inside the body via the LCST material. In general, other PEO-PPO block copolymers that are LCST materials and that are biocompatible, biodegradable, and exist as a gel at body temperature and a liquid at below body temperature can also be used according to the present invention. The molecular weight of a suitable material (such as a block copolymer) can be, for example, between 5,000 and 25,000, and more particularly between 7,000 and 15,000, and, for the two specific compounds identified above, 12,600 or 14,600.

Referring to FIG. 1a, distal end of a guide wire 108 is inserted into the urinary tract until reaching the kidney 100. The guide wire 108 can include a controllable tip for the purpose of directing the guide wire 108 along the urinary tract. The guide wire 108 could similarly be inserted into other tracts or passageways of the body. A stone 106 is present in the calyx 102 of the kidney 100. The stone 106 could also be located in other locations of the kidney 100 such as the renal pelvis or other locations in the urinary tract such as the ureter 104.

Figure 1B:
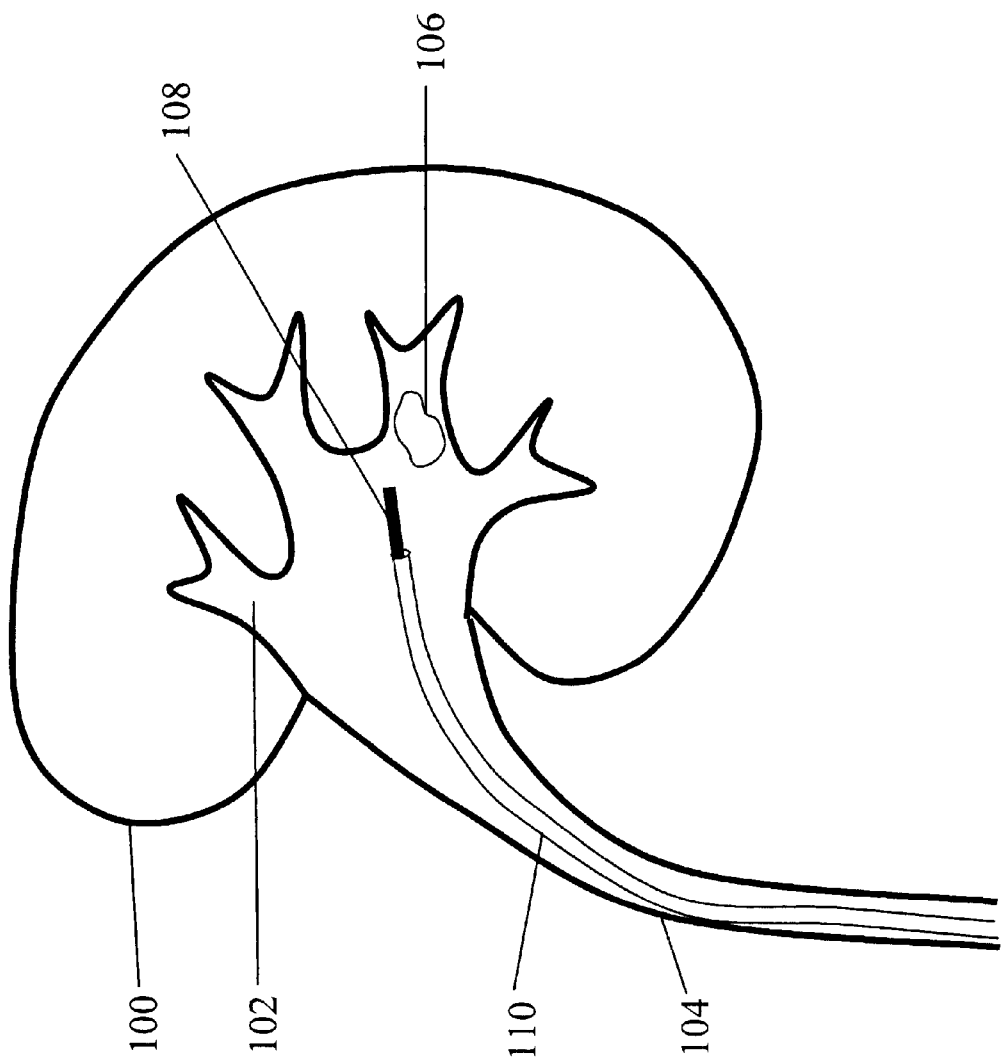

In FIG. 1b, the guide wire 108 serves as a guide for the insertion of the distal end of the catheter 110 into the kidney 100. The catheter 110 slides over the guide wire 108 with the guide wire 108 located in the lumen of the catheter 110. The catheter 110 may extend into the kidney so that the distal end of the catheter 110 is disposed near the kidney calyx 102 and the stone 106.

The guide wire 108 is then withdrawn from the lumen of the catheter 110 and is removed from the body, thus leaving the catheter 110 within the body. The LCST material 112 starts external to the body and thus at a temperature below body temperature and in a liquid and flowable form. In some embodiments, the LCST material 112 could be cooled to a temperature below ambient air temperature prior to injection to delay the time required for the injected LCST material 112 to reach body temperature and form a gel, but such cooling generally is not required. A mechanism, such as an automated or human-operated syringe, can be used to force the LCST material 112 through the catheter 110 and into the kidney 100, as shown in FIG. 1c. The mechanism can be any suitable device that applies pressure to the LCST material 112 to force it in a liquid form through the catheter 110 and into the body to contact the object to be stabilized. The LCST material 112 then enters, as a liquid, areas of the kidney 100 including the calyx 102 and the renal pelvis. The LCST material 112 also generally flows into the ureter 104 and towards the urinary bladder, as depicted in FIG. 1c. As the temperature of the LCST material 112 inside the body rises toward body temperature, the LCST material 112 reaches its LCST and transitions into the gel phase. An object, like the stone 106, in contact with the LCST material 112 will be at least partially enveloped by the gel and thus stabilized by the gel. The stabilization of the stone 106 allows for easier capture and retrieval of the stone 106 because the stone 106 is held in place by the gel 112. Additionally, the transition from liquid to gel can cause the LCST material 112 to form a seal or plug in the ureter 104 near the renal pelvis that allows the LCST material 112 to accumulate in the kidney 100 instead of draining out of the ureter 104.

Figure 1D:
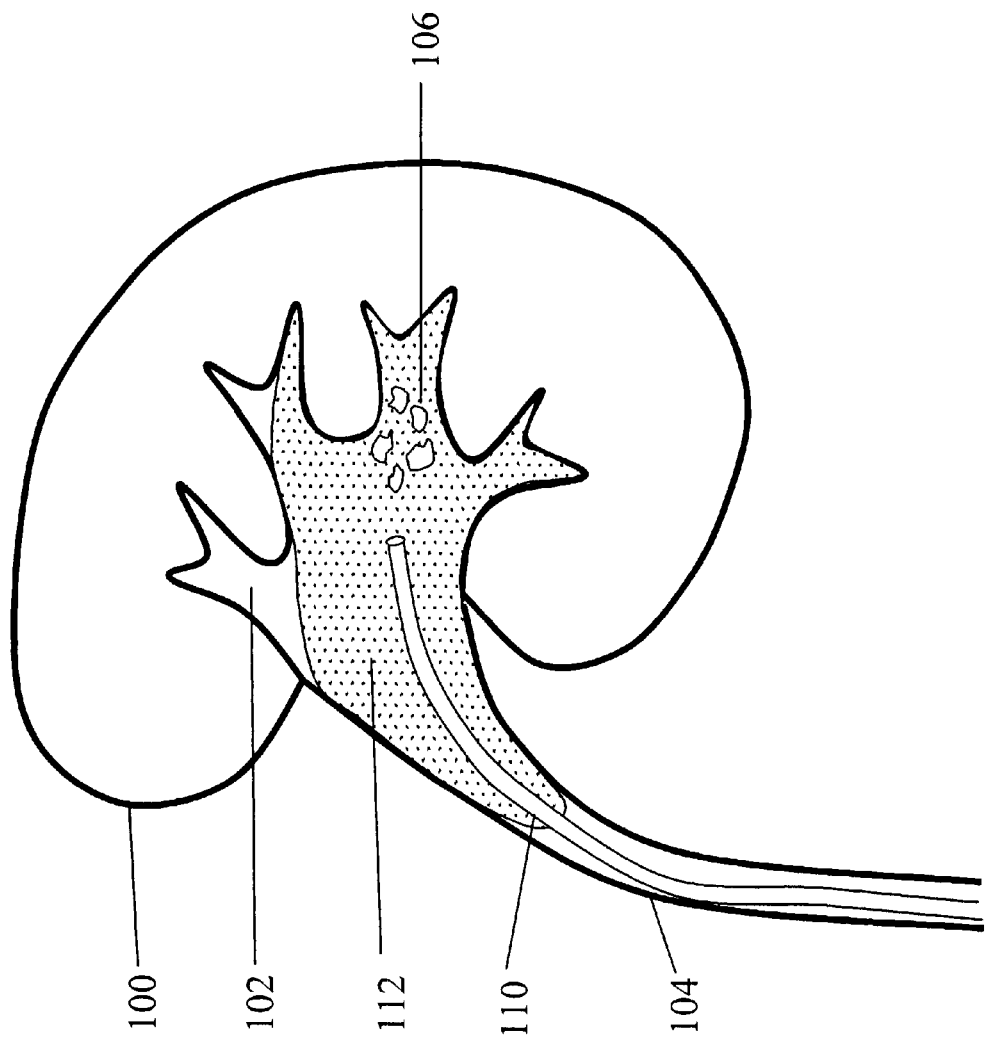
FIG. 1d is similar to FIG. 1c except that FIG. 1d shows the kidney stone after being fragmented by, for example, a medical lithotripsy device.

In FIG. 1d, the stone 106 is shown broken apart into fragments, and this fragmentation can be achieved by a medical device that delivers light, chemical, physical, or other type of energy to the stone 106. Following the breaking apart of the stone 106, the fragments of the stone 106 do not disperse throughout areas of the kidney. The gel formed from the LCST material 112 generally does not allow the fragments to escape, and the gel retains and stabilizes the fragments. The gel generally absorbs at least some of the energy imparted to the stone 106 to cause it to break apart, and thus the gel prevents the fragments of stone 106 and the stone 106 itself from dispersing throughout the kidney 100. The step of breaking apart the stone 106 is not required for the application of the methods or systems of the present invention.

In FIG. 1e, a fragment or a whole stone 106 is captured by a medical retrieval device 114. The retrieval device 114 may be inserted into the kidney 100 via the urinary tract or through the catheter 110 or in some other manner. The retrieval device 114 can be a basket. The basket or other stone capturing device makes contact with the stone 106 and typically is manipulated by a human operator to ensnare the stone 106. Once the stone 106 is captured, the device 114 can be withdrawn from the body in order to remove the stone 106. The capture and removal of stones 106 or stone fragments can be repeated by reinserting the retrieval device 114. The LCST material that forms the gel functions to stabilize the stones 106 or stone fragments during the possible multiple rounds of stone removal thus preventing dispersal of stones 106 or stone fragments throughout the kidney 100.

In FIG. 1f, the retrieval device 114 has been withdrawn from the kidney 100. The LCST material 112 in gel form will break down and flush out of the body over time. To speed the removal of the gel from the body, a chilled fluid can be introduced into the body, but such a procedure generally is not required. If used, the fluid could be a physiologically-acceptable liquid such as water, saline, contrast media, or other fluid having temperature below the LCST of the LCST material 112. The preferred temperature of the chilled fluid is, for example, −10° C. to 20° C., and more preferably 0° C. to 10° C. The fluid may be chilled by packing the fluid in ice, refrigerating the fluid or other means. The fluid could be introduced into the gel 112 through the catheter 110. The catheter 110 can be used to remove (by, for example, suction) at least some of the LCST material 112, whether or not the gel is cooled to return it to its flowable liquid form. In one preferred embodiment, a cooling fluid is not used in either the delivery or removal of the LCST material, and instead the gel is eliminated naturally from the body over time. The catheter 110 could be an independent tubular structure as shown. Alternatively, catheter 110 could be incorporated as part of a medical device that is inserted into the kidney 100 such as a tool that breaks apart the stone 106 or collects stone fragments.

Figure 2A:
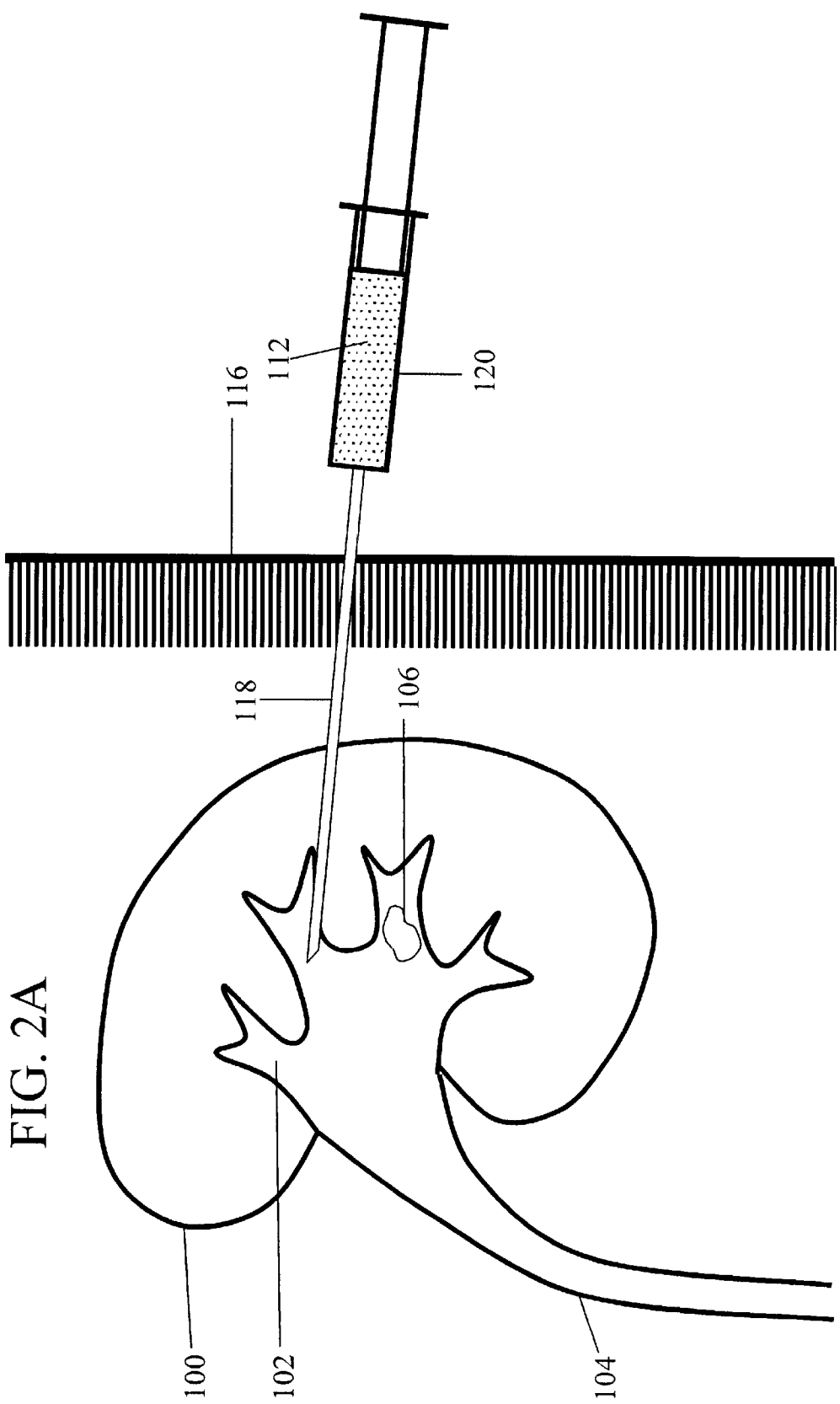
FIG. 2a illustrates the percutaneous insertion of a needle into a kidney containing a kidney stone, with a syringe containing an LCST material connected to the needle on the outside of the patient's body.

FIGS. 2a–e generally depict methods and systems of the invention that are similar to the methods and systems depicted in FIGS. 1a–f. The primary difference between the two sets of drawings is the way the LCST material 112 is introduced into the body. Referring to FIG. 2a, a needle 118 is inserted percutaneously through the skin 116 and into the body of the patient through the wall of the kidney 100 until reaching the calyx 102. A stone 106 is present in the calyx 102 of the kidney 100. The stone 106 could also be located in other locations of the kidney 100 such as the renal pelvis or other locations in the urinary tract such as the ureter 104.

The LCST material 112 starts external to the body and thus at a temperature below body temperature and in a liquid and flowable form. In some embodiments, the LCST material 112 could be cooled to a temperature below ambient air temperature prior to injection to delay the time required for the injected LCST material 112 to reach body temperature and form a gel, but such cooling generally is not required. A mechanism, such as an automated or human-operated syringe, can be used to force the LCST material 112 through the needle 118 and into the kidney 100, as shown in FIG. 2b. The mechanism can be any suitable device that applies pressure to the LCST material 112 to force it in a liquid form through the needle 118 and into the body to contact the object to be stabilized. The LCST material 112 then enters, as a liquid, areas of the kidney 100 including the calyx 102 and the renal pelvis. The LCST material 112 also generally flows into the ureter 104 and towards the urinary bladder, as depicted in FIG. 2b. As the temperature of the LCST material 112 inside the body rises toward body temperature, the LCST material 112 reaches its LCST and transitions into the gel phase. An object, like the stone 106, in contact with the LCST material 112 will be at least partially enveloped by the gel and thus stabilized by the gel. The stabilization of the stone 106 allows for easier capture and retrieval of the stone 106 because the stone 106 is held in place by the gel 112. Additionally, the transition from liquid to gel can cause the LCST material 112 to form a seal or plug in the ureter 104 near the renal pelvis that allows the LCST material 112 to accumulate in the kidney 100 instead of draining out of the ureter 104.

Figure 2C:
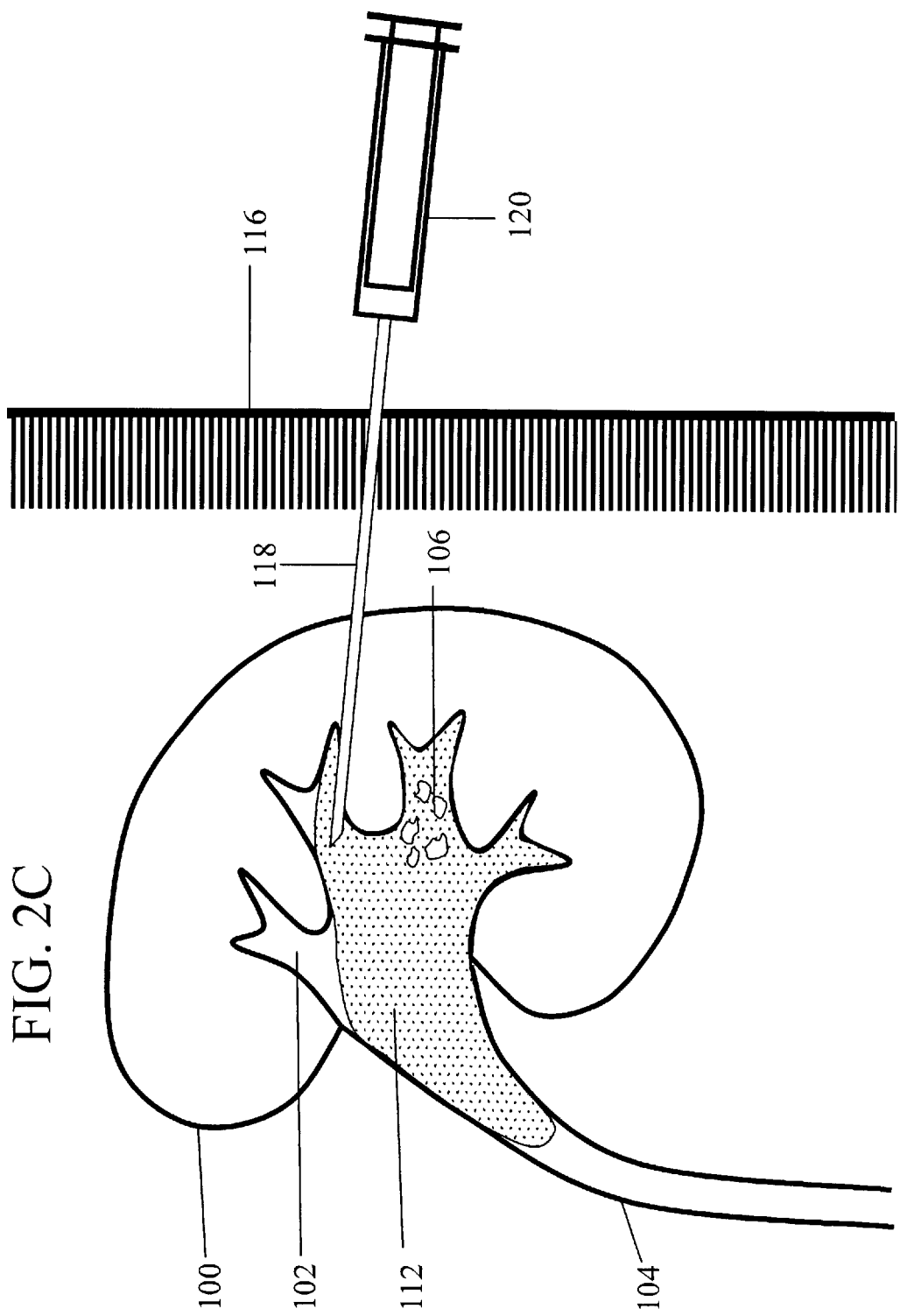
FIG. 2c shows the kidney stone after being fragmented by, for example, a medical lithotripsy device.

In FIG. 2c, the stone 106 is shown broken apart into fragments, and this fragmentation can be achieved by a device that delivers light, chemical, physical, or other type of energy to the stone 106. Following the breaking apart of the stone 106, the fragments of the stone 106 do not disperse throughout areas of the kidney. The gel formed from the LCST material 112 generally does not allow the fragments to escape, and the gel, retains and stabilizes the fragments. The gel generally absorbs at least some of the energy imparted to the stone 106 to cause it to break apart, and thus the gel prevents the fragments of stone 106 and the stone 106 itself from dispersing throughout the kidney 100. The step of breaking apart the stone 106 is not required for the application of the methods or systems of the present invention.

Figure 2D:
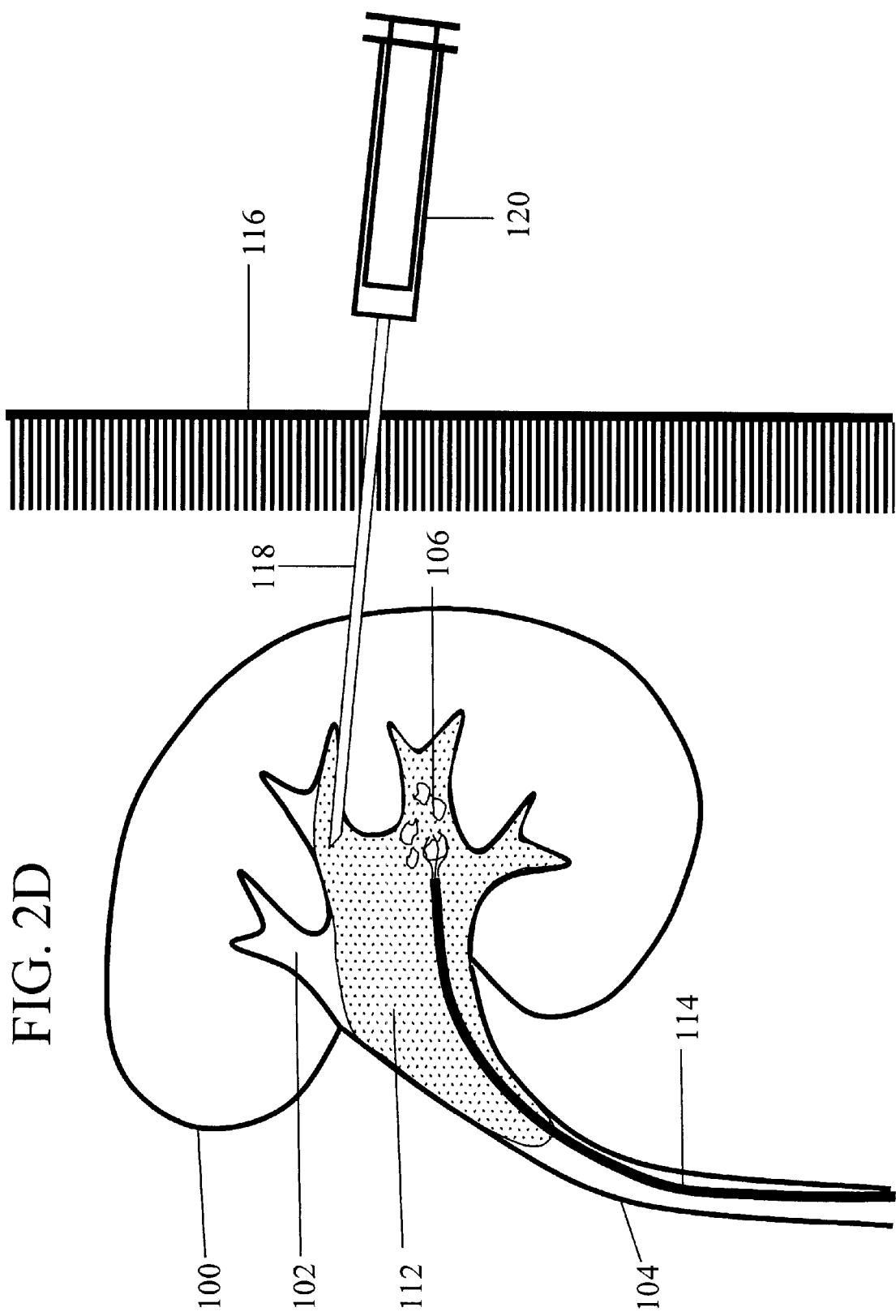
FIG. 2d illustrates the capture of a kidney stone fragment by a medical retrieval device such as a basket.

In FIG. 2d, a fragment or a whole stone 106 is captured by a medical retrieval device 114. The retrieval device 114 may be inserted into the kidney 100 via the urinary tract or through the catheter 110 or in some other manner. The retrieval device 114 can be a basket. The basket or other stone capturing device makes contact with the stone 106 and typically is manipulated by a human operator to ensnare the stone 106. Once the stone 106 is captured, the device 114 can be withdrawn from the body in order to remove the stone 106. The capture and removal of stones 106 or stone fragments can be repeated by reinserting the retrieval device 114. The LCST material that forms the gel functions to stabilize the stones 106 or stone fragments during the possible multiple rounds of stone removal thus preventing dispersal of stones 106 or stone fragments throughout the kidney 100.

Figure 2E:
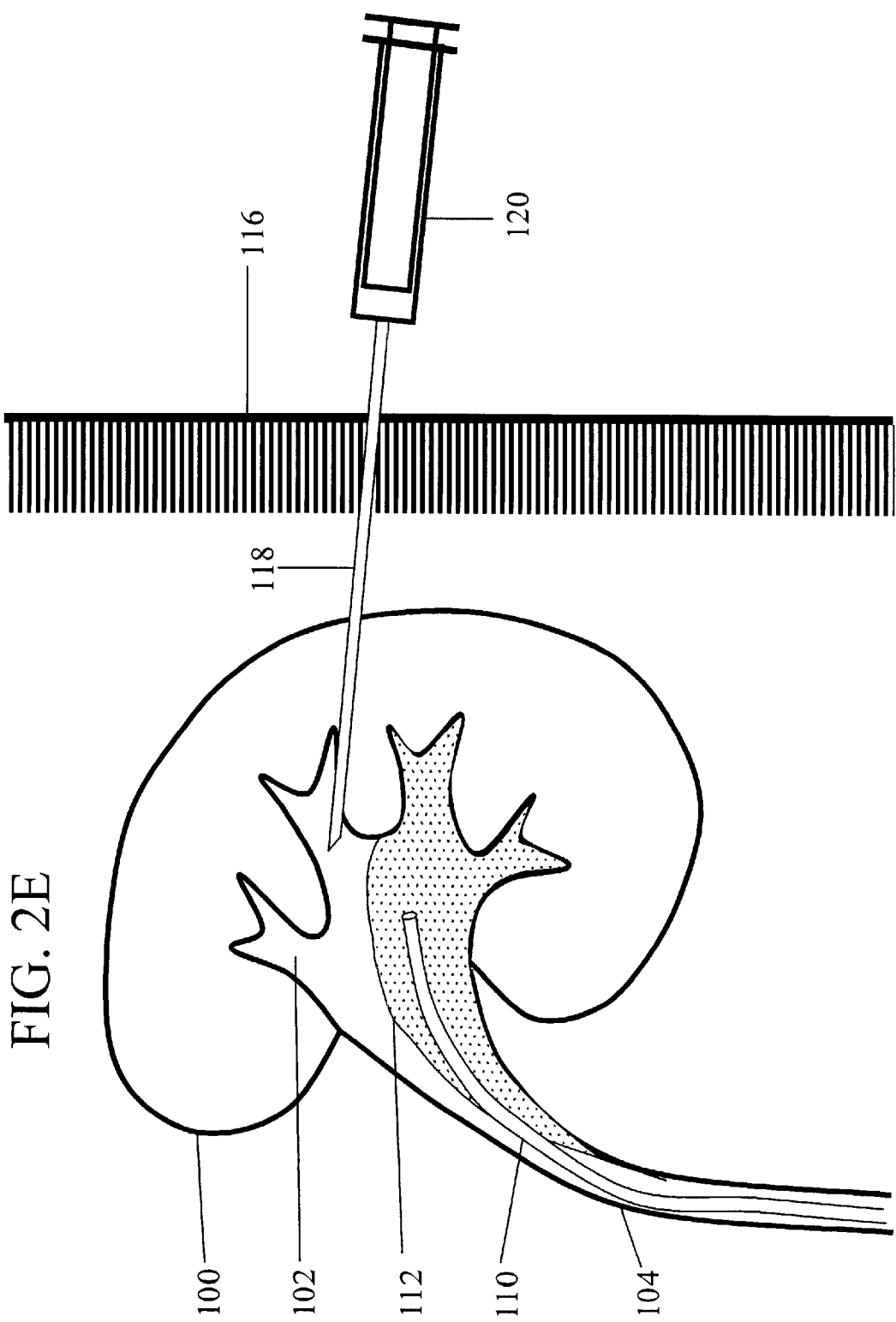
FIG. 2e shows the kidney after removal of the kidney stone fragments and after some of the LCST material has drained and/or been removed from the body.

In FIG. 2e, the retrieval device 114 has been withdrawn from the kidney 100. The LCST material 112 in gel form will break down and flush out of the body over time. To speed the removal of the gel from the body, a chilled fluid can be introduced into the body, but such a procedure generally is not required. If used, the fluid could be a physiologically-acceptable liquid such as water, saline, contrast media, or other fluid having temperature below the LCST of the LCST material 112. The preferred temperature of the chilled fluid is, for example, −10° C. to 20° C., and more preferably 0° C. to 10° C. The fluid may be chilled by packing the fluid in ice, refrigerating the fluid or other means. The fluid could be introduced into the gel 112 through the needle 118. Additionally, a catheter 110 can be used to remove (by, for example, suction) at least some of the LCST material 112, whether or not the gel is cooled to return it to its flowable liquid form. In one preferred embodiment, a cooling fluid is not used in either the delivery or removal of the LCST material, and instead the gel is eliminated naturally from the body over time. The needle 118 could be an independent tubular structure as shown. Alternatively, needle 118 could be incorporated as part of a medical device that is inserted into the kidney 100 such as a tool that breaks apart the stone 106 or collects stone fragments.

The LCST material 112 used to stabilize an object in the body can also function as a carrier for chemical compounds, drugs, hormones, dyes or other additives to enhance the effectiveness, safety or functionality of the gel. The LCST gel mixture may include a dye to aid in determining the presence of the LCST material. The LCST gel mixture can also include antibiotics and anti-microbial agents, and such a mixture may assist in protecting the kidney against infection as a result of an invasive surgical procedure. The LCST gel mixture can also include one or more anti-inflammatory agents which may assist in preventing inflammation in the kidney as a result of an invasive surgical procedure. Anesthetic agents may also be included in the LCST mixture in order to assist in numbing the pain associated with the surgical procedure. The LCST material can also contain therapeutic agents. The therapeutic agents may include anti-angiogenic agents such as endostatin, angiostatin and thrombospondin. A LCST mixture containing anti-angiogenic agents could be used to treat cancerous tumors.

The catheter 110 can be used to dispense one or more fluids other than or in addition to the LCST material. The catheter 110 also can be a dilatation catheter with the ability also to dispense one or more fluids other than or in addition to the LCST material. In one embodiment, the catheter 110 is 4–8 french in size, and more preferably 5–6 french.

The syringe or other mechanism used to inject the LCST material in liquid form into the body can be, for example, a 5–100 cc syringe such as a syringe with volume of 5–30 cc or with a volume of 5–10 cc. Pressure applied to the syringe can be applied by hand or by an automated syringe pusher.

While the invention has been described above mainly in connection with the stabilization and then removal and/or fragmentation of a kidney stone, the invention has applicability to object stabilization, removal, and fragmentation generally. A variety of stones and other objects, other than kidney stones, can be acted on in accordance with the invention, such as gall stones and biliary stones. Also, a variety of locations within the body of a patient-can be accessed and treated according to the invention, such as other parts of the male or female urinary system, the gastrointestinal system, the biliary system, and the pancreatic duct.

It will be apparent to those skilled in the art that various modifications and variations can be made to the above-described structure and methodology without departing from the scope or spirit of the invention.

What is claimed is:

1. A method of stabilizing and eliminating an object in the body of a patient, comprising:
    injecting a lower critical solution temperature material in a flowable form into the body of the patient to contact the object;
    allowing the lower critical solution temperature material to form a gel in the body such that the object is contained at least partially within the gel and thereby stabilized by the gel, the material existing as the gel at temperatures about at and above a temperature inside the body of the patient; and
    retrieving, breaking, or otherwise eliminating the object from the body.

2. The method of claim 1 wherein the lower critical solution temperature material remains in the flowable form below about the temperature inside the body of the patient.

3. The method of claim 2 wherein the lower critical solution temperature material comprises a block copolymer with reverse thermal gelation properties.

4. The method of claim 3 wherein the block copolymer comprises a polyoxyethylene-polyoxypropylene block copolymer.

5. The method of claim 4 wherein the block copolymer has a molecular weight in the range of about 5,000 to about 25,000.

6. The method of claim 3 wherein the block copolymer comprises a biodegradable, biocompatible copolymer of polyethylene oxide and polypropylene oxide.

7. The method of claim 1 further comprising the step of retrieving the stabilized object from the gel.

8. The method of claim 1 wherein the object comprises a kidney stone.

9. The method of claim 1 further comprising the step of breaking the object into at least two fragments, at least some of the at least two fragments remaining at least partially within the gel and stabilized by the gel.

10. The method of claim 9 further comprising the step of retrieving the at least some of the at least two fragments from the gel.

11. The method of claim 1 wherein the lower critical solution temperature material includes a therapeutic agent.

12. The system of claim 11 wherein the therapeutic agent comprises an anti-angiogenic agent.

13. A system for stabilizing an object formed of a natural or foreign biological material in the body of a patient, comprising:
    a lower critical solution temperature material which remains in a flowable form below about a temperature inside the body of the patient and which exists as a gel at temperatures about at and above the temperature inside the body of the patient;

a catheter for transferring the lower critical solution temperature material into the body in the flowable form;

a guide wire for introducing the catheter into the body and guiding it to about the location of the object; and a mechanism to force the lower critical solution temperature material in the flowable form through the catheter and into the body to contact the object such that the lower critical solution temperature material gels in the body due to the temperature inside the body and contains at least a portion of the object within the gel to stabilize the object with the gel.

14. The system of claim 13 wherein the catheter also is utilized in removing the lower critical solution temperature material from the body.

15. The system of claim 13 wherein the mechanism comprises a syringe.

16. The system of claim 13 wherein the lower critical solution temperature material comprises a block copolymer with reverse thermal gelation properties.

17. The system of claim 16 wherein the block copolymer comprises a polyoxyethylene-polyoxypropylene block copolymer.

18. The system of claim 17 wherein the block copolymer has a molecular weight in the range of about 5,000 to about 25,000.

19. The system of claim 16 wherein the block copolymer comprises a biodegradable, biocompatible copolymer of polyethylene oxide and polypropylene oxide.

20. The system of claim 13 wherein the object comprises a kidney stone.

21. The system of claim 13 wherein the lower critical solution temperature material includes a therapeutic agent.

22. The system of claim 21 wherein the therapeutic agent comprises an anti-angiogenic agent.

23. A system for stabilizing an object formed of a natural or foreign biological material in the body of a patient, comprising:

a lower critical solution temperature material which remains in a flowable form below about a temperature inside the body of the patient and which exists as a gel at temperatures about at and above the temperature inside the body of the patient;

a percutaneous access device for transferring the lower critical solution temperature material into the body in the flowable form; and a mechanism to force the lower critical solution temperature material in the flowable form through the percutaneous access device and into the body to contact the object such that the lower critical solution temperature material gels in the body due to the temperature inside the body and contains at least a portion of the object within the gel to stabilize the object with the gel.

24. The system of claim 23 wherein the percutaneous access device comprises a needle.

25. The system of claim 23 further comprising a catheter for removing the lower critical solution temperature material from the body.

26. The system of claim 23 wherein the mechanism comprises a syringe.

27. The system of claim 23 wherein the lower critical solution temperature material comprises a block copolymer with reverse thermal gelation properties.

28. The system of claim 27 wherein the block copolymer comprises a polyoxyethylene-polyoxypropylene block copolymer.

29. The system of claim 28 wherein the block copolymer has a molecular weight in the range of about 5,000 to about 25,000.

30. The system of claim 27 wherein the block copolymer comprises a biodegradable, biocompatible copolymer of polyethylene oxide and polypropylene oxide.

31. The system of claim 23 wherein the object comprises a kidney stone.

32. The system of claim 23 wherein the lower critical solution temperature material includes a therapeutic agent.

33. The system of claim 32 wherein the therapeutic agent comprises an anti-angiogenic agent.

34. A system for stabilizing an object formed of a natural or foreign biological material in the body of a patient, comprising:

a lower critical solution temperature material which remains in a flowable form below about a temperature inside the body of the patient and which exists as a gel at temperatures about at and above the temperature inside the body of the patient;

a catheter for transferring the lower critical solution temperature material into the body in the flowable form; and a mechanism to force the lower critical solution temperature material in the flowable form through the catheter and into the body to contact the object such that the lower critical solution temperature material gels in the body due to the temperature inside the body and contains at least a portion of the object within the gel to stabilize the object with the gel.

35. The system of claim 34 wherein the catheter also is utilized in removing the lower critical solution temperature material from the body.

36. The system of claim 34 wherein the mechanism comprises a syringe.

37. The system of claim 34 wherein the lower critical solution temperature material comprises a block copolymer with reverse thermal gelation properties.

38. The system of claim 37 wherein the block copolymer comprises a polyoxyethylene-polyoxypropylene block copolymer.

39. The system of claim 37 wherein the block copolymer comprises a biodegradable, biocompatible copolymer of polyethylene oxide and polypropylene oxide.

* * * * *